United States Patent [19]

Thies et al.

[11] 4,391,819

[45] Jul. 5, 1983

[54] 2,9-DIOXA TRICYCLO [4,3,1,0³·⁷] DECANE COMPOUNDS AND PROCESS OF MAKING SAME

[75] Inventors: Peter W. Thies; Samuel David, both of Hanover, Fed. Rep. of Germany

[73] Assignee: Kali-Chemie Pharma GmbH, Hanover, Fed. Rep. of Germany

[21] Appl. No.: 283,104

[22] Filed: Jul. 13, 1981

[30] Foreign Application Priority Data

Jul. 14, 1980 [DE] Fed. Rep. of Germany ....... 3026579

[51] Int. Cl.³ .................... A61K 31/335; C07D 405/06
[52] U.S. Cl. .................................... 424/278; 549/281; 549/420
[58] Field of Search ...................... 260/340.3; 549/281; 424/278

[56] References Cited

U.S. PATENT DOCUMENTS 3,812,154  5/1974  Thies ................................ 260/340.3
4,163,055  7/1979  Thies et al. ....................... 260/340.3

FOREIGN PATENT DOCUMENTS 2305085  8/1973  Fed. Rep. of Germany ... 260/340.3

OTHER PUBLICATIONS

*Tetrahedron Letters, 1970,* Peter W. Thies *"Stereochemie des didrovaltratum und synthese einiger 2,9-dioxatricyclo. . . "* pp. 3087-3090 No. 35.

*Primary Examiner*—Ethel G. Love

*Attorney, Agent, or Firm*—Schwartz, Jeffery, Schwaab, Mack, Blumenthal & Koch

[57] ABSTRACT

Novel and highly effective sleep inducing 3β-hydroxy methyl-4α-hydroxy-8β-alkoxy-2,9-dioxa tricyclo [4,3,1,0³·⁷] decane compounds of the following Formula:

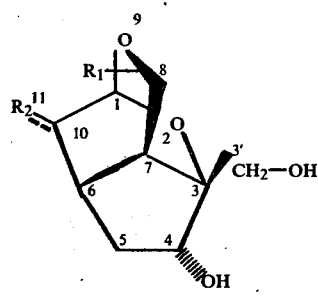

in which $R_1$ indicates an alkoxy group and preferably a lower alkoxy group, such as the methoxy group, the ethoxy group, or the n-butoxy group, while $R_2$ indicates the 10-methylene group or the 10β-methyl group, are produced from didrovaltratum, i.e., 1-isovaleroxy-4-isovaleroxy methyl-7-acetoxy-spiro-oxirano-1,9-dihydrocyclopenta(c)pyrane or from extracts of plants of the genus Valerianaceae which contain about 70% of didrovaltratum. The novel compounds have a surprisingly low toxicity.

11 Claims, No Drawings

2,9-DIOXA TRICYCLO [4,3,1,0³,⁷] DECANE COMPOUNDS AND PROCESS OF MAKING SAME

BACKGROUND OF THE INVENTION

1. Field of the Invention

The present invention relates to novel and advantageous 8β-substituted 3β-hydroxy methyl-4α-hydroxy-2,9-dioxa tricyclo[4,3,1,O³,⁷]decane compounds and more particularly to valuable and highly effective, pharmaceutically useful 3β-hydroxy methyl-4α-hydroxy-8β-alkoxy-10-methylene-2,9-dioxa tricyclo[4,3,1,O³,⁷]decanes of the following Formula I

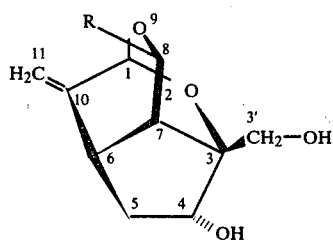

In said Formula

R indicates an alkoxy group and preferably a lower alkoxy group.

The 10,11-double bond may be hydrogenated. The present invention also relates to simple and effective processes of producing such compounds of Formula I, to pharmaceutical compositions containing such compounds, and to a method of using said compounds as sleep inducing and improving agents.

2. Description of the Prior Art

In a number of prior applications there are described 2,9-dioxa tricyclo[4,3,1,O³,⁷]decane compounds which are distinguished by their advantageous pharmacological properties and more particularly by their novel action upon the central nervous system. German Published Application No. 26 07 106 describes compounds of this type which have sleep promoting properties. These effects on sleeping, evidenced by an improvement of the deep sleep (quiet sleep) as well as of the paradoxal sleep (rapid eye movement sleep), apparently are due to the presence of an amino methyl group in 3-position in the 2,9-dioxa tricyclo[4,3,1,O³,⁷]decane ring system, in contrast to other known 2,9-dioxa tricyclo[4,3,1,O³,⁷]decane compounds which have a methyl, a halogeno methyl, or, respectively, an azido methyl group in 3-position.

SUMMARY OF THE INVENTION

It is one object of the present invention to provide new 2,9-dioxa tricyclo[4,3,1,O³,⁷]decane compounds with improved pharmacological properties, which compounds are favorably distinguished over known compounds of this type by an improved profile of activity and, more particularly, by a pronounced sleep inducing effect.

Another object of the present invention is to provide simple and effective processes of producing such novel and pharmacologically highly effective 2,9-dioxa tricyclo[4,3,1,O³,⁷]decane compounds.

A further object of the present invention is to provide pharmaceutical compositions containing said novel 2,9-dioxa tricyclo[4,3,1,O³,⁷]decane compounds with a surprising sleep inducing activity.

Still another object of the present invention is to provide a method of using said novel 2,9-dioxa tricyclo[4,3,1,O³,⁷]decane compounds for their sleep inducing properties.

Other objects of the present invention and advantageous features thereof will become apparent as the description proceeds.

In principle it was found that pharmacologically highly effective 2,9-dioxa tricyclo[4,3,1,O³,⁷]decane compounds with an astonishingly high sleep inducing activity are characterized by having a 3-hydroxy methyl group in place of the 3-methyl group, the 3-halogeno methyl group, the 3-azido methyl group, or, respectively, the 3-amino methyl group. More particularly the novel 3-hydroxy methyl-2,9-dioxa tricyclo[4,3,1,O³,⁷]decane compounds according to the present invention are 3β-hydroxy methyl-4α-hydroxy-8β-alkoxy-2,9-dioxa-tricyclo[4,3,1,O³,⁷]decane compounds of Formula I:

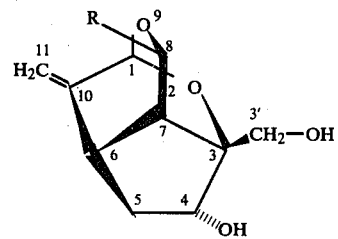

In said Formula I

R indicates an alkoxy group, preferably a lower alkoxy group, and more advantageously an alkoxy group with 1 to 4 carbon atoms, and in which the double bond between the carbon atoms 10 and 11 can be hydrogenated, the substituent in 10-position thus being the 10-methylene group or, respectively, the 10β-methyl group.

Preferred examples of novel and highly effective compounds according to the present invention are the following compounds:

3β-hydroxy methyl-4α-hydroxy-8β-methoxy-10-methylene-2,9-dioxa tricyclo[4,3,1,O³,⁷]decane, 3β-hydroxy methyl-4α-hydroxy-8β-methoxy-10β-methyl-2,9-dioxa tricyclo[4,3,1,O³,⁷]decane, 3β-hydroxy methyl-4α-hydroxy-8β-ethoxy-10-methylene-2,9-dioxa tricyclo[4,3,1,O³,⁷]decane, 3β-hydroxy methyl-4α-hydroxy-8β-ethoxy-10β-methyl-2,9-dioxa tricyclo[4,3,1,O³,⁷]decane, and 3β-hydroxy methyl-4α-hydroxy-8β-butoxy-10β-methyl-2,9-dioxa tricyclo[4,3,1,O³,⁷]decane.

These and other compounds of Formula I according to the present invention inhibit motor activity and have a pronounced sleep inducing effect as can be shown on the electro-encephalogram (EEG) of rats. Within three hours after administration, these compounds show a more extensive and pronounced effect on decreasing wakefulness than during the five subsequent hours, so that there is substantially no danger of a "hang-over" in humans.

Thus, for instance, the 3β-hydroxy methyl-4α-hydroxy-8β-methoxy-10β-methyl-2,9-dioxa tricyclo[4,3,1,O³,⁷]decane causes already with a dosage of 0.8 mg./kg. a pronounced inhibition of motor activity with mice when tested in the light beam barrier cage (photo cell cage). The dosage which causes a sleep inducing effect in rats determined by the three hour electro-encephalogram (EEG) amounts to about 2.5 mg./kg. The toxicity determined by intraperitoneal administration to mice is extremely favorable, i.e. exceeds 1,600 mg./kg.(LD$_{50}$).

The innovative structure of the compounds according to the present invention, their compatibility, as well as their high effectiveness as sleep inducing agents meet a great demand for a novel soporific or hypnotic agent.

The compounds according to the present invention are prepared by following stereochemically highly selective procedures. Several variations of these processes are illustrated by the attached diagrammatic formula flow-sheet.

The formula flow-sheet is based on the preparation of the 3$\beta$-hydroxy methyl-4$\alpha$-hydroxy-8$\beta$-methoxy-10$\beta$-methyl-2,9-dioxa tricyclo[4,3,1,O$^{3,7}$]decane. It is, of course, understood that the procedures illustrated by said flow-sheet and described hereinafter are not limited to the production of the last mentioned compound, but can be varied and used also for the production of other compounds according to the present invention as it will be shown and described hereinafter in the examples.

The starting material for all these compounds and in all these process variations is didrovaltratum, i.e. 1-isovaleroxy-4-isovaleroxy methyl-7-acetoxy-8-spiro-oxirano-1,9-dihydrocyclopenta(c)pyrane.

A total extract of plants of the genus Valerianaceae which contains about 70% of didrovaltratum can also be used.

According to one variation of the processes of the present invention, i.e. process steps 1.0 to 1.5 of the formula flow sheet, the starting didrovaltratum (Formula 1.0) is converted by means of a mixture of glacial acetic acid and acetic acid anhydride into the corresponding acetohydrin (Formula 1.1). Thereupon the acetohydrin is converted by the action of methanol and p-toluene sulfonic acid into the 3$\beta$-acetoxy methyl-4$\beta$-acetoxy-8$\beta$-methoxy-10-methylene-2,9-dioxa tricyclo[4,3,1,O$^{3,7}$]decane (Formula 1.2).

These two reaction steps are already described in Published German Application No. 19 61 433. When using other alcohols in place of methanol, as mentioned in said German application, there are obtained, depending upon the respective alcohol used, the corresponding 8-alkoxy compounds as this is also known from said German application.

After saponification of both acetoxy groups in said reaction products (Formula 1.2), for instance, by means of aqueous or aqueous-alcoholic alkali metal hydroxide solution or by means of potassium carbonate in methanol, the corresponding dihydroxy compound is obtained. If the 10$\beta$-methyl compound is to be produced as final product, as this is shown in the formula flow-sheet, the reaction is carried out, for instance, by simultaneously hydrogenating the 10,11-double bond, for instance, by means of hydrogen in the presence of a Raney-nickel catalyst, and a strong inorganic base. Thereby the two acetoxy groups are saponified at the same time and the dihydroxy compound with a methyl group in 10$\beta$-position of Formula 1.3 is produced.

Thereupon, the 4$\beta$-hydroxyl group is selectively oxidized, for instance, by means of chromium trioxide, preferably by means of pyridinium chloro chromate to the corresponding ketone (Formula 1.4).

Finally the resulting 4-one compound is selectively reduced by means of complex metal hydrides, for instance, by means of lithium aluminum hydride and preferably by means of sodium boronhydride, to the desired 4$\alpha$-hydroxy final compound (Formula 1.5).

According to the process variation 2 as illustrated on the formula flow-sheet, dihydrovaltratum (Formula 1.0) is converted by means of hydrogen iodide in methanol directly into the 3$\beta$-iodo methyl-4$\beta$-acetoxy-8$\beta$-methoxy-10-methylene-2,9-dioxa tricyclo[4,3,1,O$^{3,7}$]decane (Formula 2.1). This reaction is known per se from Published German Application No. 21 29 507. According to said application it is also possible to obtain, depending upon the alcohol used and the hydrogen halide employed, the corresponding 8$\beta$-alkoxy-3$\beta$-halogeno methyl compounds.

Depending upon whether the 10$\beta$-methyl compound or the 10-methylene compound are to be obtained as final products, the 10,11-double bond can be hydrogenated by means of hydrogen in the presence of platinum oxide to the 10$\beta$-methyl group, as this is known from the Published German Application No. 27 19 916. Either the resulting 10$\beta$-methyl compound (Formula 2.2) or, if desired, the 10-methylene compound (Formula 2.1) is saponified, for instance, by means of aqueous or aqueous-alcoholic alkali metal hydroxide solution or by means of potassium carbonate in methanol to the corresponding 3$\beta$-iodo methyl-4$\beta$-hydroxy compound (Formula 2.3). Said compound is then oxidized to the corresponding decane-4-one compound (Formula 2.4), for instance, by means of Jones reagent and preferably by means of pyridinium chloro chromate. Thereupon, the 3$\beta$-iodo methyl group of the resulting ketone compound (Formula 2.4) is converted into the 3$\beta$-acetoxy methyl group of the compound of Formula 2.5, for instance, by means of sodium or potassium acetate preferably in the presence of quaternary alkyl ammonium acetates such as, for instance, tetra-ethyl or tetrabutyl ammonium acetate. Finally the 4-keto group in the resulting 3$\beta$-acetoxy methyl compound (Formula 2.5) is reduced to the 4$\alpha$-hydroxyl group by means of complex metal hydrides, such as lithium aluminum hydride. When using lithium aluminum hydride as reducing agent, the 3$\beta$-acetoxy methyl group is at the same time converted into the 3$\beta$-hydroxy group to yield the desired dihydroxy final product of Formula 2.6 corresponding to Formula 1.5. When carrying out the reduction of the 4-keto group by means of other complex metal hydrides, for instance, by means of sodium borohydride, the 3$\beta$-acetoxy methyl group is saponified to the 3$\beta$-hydroxy methyl group subsequently to the reduction of the keto group.

According to another process variation 3, the 4$\beta$-hydroxy group of the compound of Formula 2.3 is first transformed, and thus protected, into the 4-(2'-tetrahydropyranyloxy) group of the compound of Formula 3.1 by reaction with 3,4dihydro-2H-pyrane. After replacing the halogen substituent by the acetoxy group as described hereinabove, the protecting tetrahydropyrane group is again split off, for instance, by means of aqueous hydrochloric acid. The again reconstituted 4$\beta$-hydroxyl group of the resulting compound of Formula 3.2 can then be oxidized, as described hereinabove, to the 4-keto group, thereby yielding the compound of Formula 3.3 corresponding to the compound of Formula 2.5. Said compound of Formula 3.3 can then be reduced and saponified to the final 4$\alpha$-hydroxy compound of Formula 2.6 corresponding to the compound of Formula 1.5 in the manner described hereinabove.

According to a further process variation 4, the 3-iodo methyl-4-one compound of Formula 2.4 is selectively reduced to the 4α-hydroxy compound (Formula 4.1) by means of complex metal hydrides, preferably by means of sodium borohydride. Said compound is then acetylated to the 4α-acetoxy compound (Formula 4.2). Thereafter the halogen substituent of the 3β-iodo methyl group is replaced by the acetoxy methyl group in the manner described hereinabove. Thus there is obtained the diacetyl compound of Formula 4.3. By saponification of both acetoxy groups there is obtained the 3β-hydroxy methyl-4α-hydroxy compound of Formula 1.5 corresponding to the compound of Formula 2.6 and Formula 4.4.

The attached DIAGRAMMATIC FORMULA FLOW SHEET illustrates the various processes described hereinabove and more in detail in the following examples. The starting material in all these processes is the same, namely didrovaltratum of Formula 1.0.

As is evident from the formula flow sheet, process 1 proceeds through the steps yielding the compounds of the formulas 1.1, 1.2, 1.3, 1.4, and the final compound of Formula 1.5, i.e. 3β-hydroxy methyl-4α-hydroxy-8β-alkoxy-10β-methyl-2,9-dioxa tricyclo[4,3,1,O$^{3,7}$]decane.

Process 2 comprises the steps leading to the intermediate products of Formulas 2.1, 2.2, 2.3, 2.4, and 2.5 and yields the final compound of Formula 2.6 corresponding to the compound of Formula 1.5.

Process 3 comprises the steps leading to the intermediate compounds of the Formulas 2.1, 2.2, 2.3, 3.1, 3.2, and 3.3 which corresponds to the compound of Formula 2.5, and yields the final compound of Formula 2.6 corresponding to the compound of Formula 1.5.

Process 4 comprises the steps leading to the intermediate products of Formulas 2.1, 2.2, 2.3, 2.4, 4.1, 4.2, and 4.3, and finally yields the compound of Formula 4.4 corresponding to the compound of Formula 1.5.

DETAILED DESCRIPTION OF PREFERRED EMBODIMENTS

The following examples serve to illustrate the present invention without, however, limiting the same thereto. To simplify the description in these examples, the designation "dioxa tricyclo[4,3,1,O$^{3,7}$]decane" is given in the abbreviated form "DTD".

The statement "M.P.: <0° C." indicates that the respective compound is an oily compound at room temperature.

EXAMPLE 1

This example describes the procedure followed according to Process 1.

Step 1.1

Preparation of didrovaltratum acetoxy hydrin of Formula 1.1

(a) Preparation from an extract of plants of the genus Valerianaceae.

424 g. of an extract from plants of the genus Valerianaceae containing about 70% of didrovaltratum are dissolved in 310 ml. of glacial acetic acid and 31 ml. of acetic acid anhydride at 80° C. After cooling the solution to room temperature, 660 ml. of triethylamine are added thereto. The mixture is stirred at 80° C. for 2½ hours. After the reaction has been completed, the reaction mixture is diluted with water and extracted with ether. The combined organic phases are dried over sodium sulfate, filtered, and concentrated by evaporation in a vacuum.

Yield: 336 g. corresponding to 70% of the theoretical yield calculated with respect to 100% didrovaltratum.

| $C_{24}H_{36}O_{10}$ | M.P.: <0° C. |
|---|---|
| Mol. weight: 484.55 | $[α]_D^{20}$: −38° (in methanol) |

(b) Preparation from didrovaltratum.

10 g. of didrovaltratum are dissolved in 11 ml. of glacial acetic acid and 1.1 ml. of acetic acid anhydride at 80° C. After cooling the solution to 20° C., 25 ml. of triethylamine are added thereto. The resulting solution is then heated to 80° C. for 2½ hours. Thereupon the reaction solution is added to ice water and extracted with ether. The combined organic phases are dried over sodium sulfate, filtered, and concentrated by evaporation in a vacuum.

Crude yield: 9.8 g. corresponding to 85.9% of the theoretical yield.

The resulting compound is identical with the compound of Formula 1.1 obtained according to the process step 1.1 (a).

Step 1.2

Preparation of 3β-acetoxy methyl-4β-acetoxy-8β-methoxy-10-methylene-2,9-DTD of Formula 1.2

336 g. of the compound of Formula 1.1 as obtained according to the process step 1.1 (a) are dissolved in 690 ml. of methanol. 6.9 g. of p-toluene sulfonic acid are added to said solution and the mixture is heated to 60° C. for 30 minutes. Thereupon the solution is added to ice water and is extracted with ether. The combined organic phases are dried over sodium sulfate, filtered, and concentrated by evaporation in a vacuum.

Yield: 211 g. corresponding to 66% of the theoretical yield calculated for 100% didrovaltratum.

| $C_{15}H_{20}O_7$ | M.P.: <0° C. |
|---|---|
| Mol. weight: 312.35 | $[α]_D^{20}$: +45° (in methanol) |

Step 1.3

Preparation of 3β-hydroxy methyl-4β-hydroxy-8β-methoxy-10β-methyl-2,9-DTD of Formula 1.3

71.7 g. of the compound of Formula 1.2 are dissolved in methanol. 24.0 g. of sodium hydroxide dissolved in methanol and Raney-nickel catalyst are added thereto and the mixture is hydrogenated at room temperature. Thereupon the catalyst is filtered off. The filtrate is neutralized with acetic acid and is concentrated by evaporation in a vacuum. The residue is dissolved in water and extracted with ether. The combined organic phases are dried over sodium sulfate, filtered, and concentrated by evaporation in a vacuum.

Yield: 42.4 g. corresponding to 80.2% of the theoretical yield.

| $C_{11}H_{18}O_5$ | M.P.: 89–90° C. |
|---|---|
| Mol. weight: 230.26 | $[α]_D^{20}$: −32° (in methanol) |

Step 1.4

Preparation of 3β-hydroxy methyl-8β-methoxy-10β-methyl-2,9-DTD-4-one of the Formula 1.4

30 g. of the compound of Formula 1.3 are dissolved in dichloro methane. Said solution is added drop by drop, while stirring, to a suspension of 37 g. of pyridinium chloro chromate in dichloro methane. After four hours 2.5 liters of ether are added to the oxidation mixture. The resulting solution is filtered to remove the precipitated salts. The solvent is distilled off and the residue is purified by chromatography over silica gel by means of ether/n-hexane.

Yield: 17.8 g. corresponding to 60% of the theoretical yield.

| $C_{11}H_{16}O_5$ | M.P.: 97–104° C. |
|---|---|
| Mol. weight: 228.27 | $[\alpha]_D^{20}$: −61.2° (in methanol) |

Step 1.5

Preparation of 3β-hydroxy methyl-4α-hydroxy-8β-methoxy-10β-methyl-2,9-DTD of Formula 1.5

1.5 g. of the compound of Formula 1.4 are dissolved in 40 ml. of ethanol. 0.5 g. of sodium borohydride are added thereto, while stirring. After stirring for one hour, the reaction mixture is neutralized by the addition of dilute hydrochloric acid and is extracted with ether. The combined organic phases are dried over sodium sulfate, filtered, and concentrated by evaporation in a vacuum.

Yield: 1.35 g. corresponding to 89.6% of the theoretical yield.

| $C_{11}H_{18}O_5$ | M.P.: 66–70° C. |
|---|---|
| Mol. weight: 239.26 | $[\alpha]_D^{20}$: −57° (in methanol) |

EXAMPLE 2

This example describes the procedure followed according to Process 2.

Step 2.1

Preparation of 3β-iodo methyl-4β-acetoxy-8β-methoxy-10-methylene-2,9-DTD of Formula 2.1

850 g. of an extract obtained from plants of the genus valerianaceae containing about 70% of didrovaltratum are dissolved in one liter of methanol. 220 ml. of 57% hydrogen iodide dissolved in one liter of methanol are slowly added to said solution at 20° C. The reaction mixture is allowed to stand at 60° C. for two hours, while stirring.

The resulting reaction mixture is then repeatedly extracted with small amounts of—all in all—one liter of n-hexane in order to remove lipophilic components therefrom. The hexane phases are discarded. The remaining aqueous phase is diluted with five liters of water and is extracted four times, each time with three liters of ether. The aqueous phase is discarded and the ethereal phase is washed with—all in all—five liters of water, neutralized with a sodium bicarbonate solution, and dried or, respectively, clarified over sodium sulfate and activated carbon. After filtration, the filtrate is concentrated by evaporation in a vacuum until its weight remains constant. 565 g. of a yellow colored oil are obtained from which 316.9 g. of 3β-iodo methyl-4β-acetoxy-8β-methoxy-10-methylene-2,9-dioxa tricyclo[4,3,1,0$^{3,7}$]decane crystallize, corresponding to 59.5% of the theoretical yield calculated for 100% didrovaltratum used.

| $C_{13}H_{17}O_5J$ | M.P.: 104–106° C. |
|---|---|
| Mol. weight: 380.19 | $[\alpha]_D^{20}$: +68° (in methanol) |

Step 2.2

Preparation of 3β-iodo methyl-4β-acetoxy-8β-methoxy-10β-methyl-2,9-DTD of Formula 2.2

A solution of 800 g. of the compound of Formula 2.1 in 3 liters of acetic acid ethyl ester is added to a suspension of 35 g. of pre-hydrogenated platinum oxide in 300 ml. of acetic acid ethyl ester. The mixture is hydrogenated at room temperature under atmospheric pressure. Initially hydrogen is absorbed very rapidly, but at the end of the hydrogenation absorption proceeds quite slowly. After absorption of the theoretical amount of hydrogen (47.2 liters), the reaction mixture is filtered in a nitrogen atmosphere through asbestos. After concentrating the filtrate by evaporation, 804 g. of a crude product are obtained, corresponding to about 100% of the theoretical yield. 542 g. of the pure 10β-epimer compound of the Formula 2.2 are obtained on repeated recrystallization from methanol. The yield is 67% of the theoretical yield calculated for the starting compound of Formula 2.1.

| $C_{13}H_{19}JO_5$ | M.P.: 129° C. |
|---|---|
| Mol. weight: 382.19 | $[\alpha]_D^{20}$: −24.5° (in methanol) |

Step 2.3

Preparation of 3β-iodo methyl-4β-hydroxy-8β-methoxy-10β-methyl-2,9-DTD of Formula 2.3

18 g. of potassium carbonate are added to 100 g. of the compound of Formula 2.2 in 400 ml. of methanol. The resulting suspension is stirred at room temperature for two hours. Excess potassium carbonate is filtered off and the filtrate is neutralized by the addition of aqueous acetic acid. After extraction with dichloro methane, the combined organic phases are dried over sodium sulfate, filtered, and concentrated by evaporation in a vacuum.

Yield: 69.37 g. of the compound of Formula 2.3, corresponding to 82.6% of the theoretical yield are obtained.

| $C_{11}H_{17}O_4J$ | M.P.: 92–93° C. |
|---|---|
| Mol. weight: 340.166 | $[\alpha]_D^{20}$: −35.3° (in methanol) |

Step 2.4

Preparation of 3β-iodo methyl-8β-methoxy-10β-methyl-2,9-DTD-4-one of Formula 2.4

8 g. of the compound of Formula 2.3 in dichloro methane are added drop by drop to a suspension of 15 g. of pyridinium chloro chromate in dichloro methane, while stirring vigorously. 400 ml. of ether are added thereto after 3 hours. The precipitated salts are filtered off and are washed with ether. The combined organic phases are concentrated by evaporation in a vacuum. The residue is purified chromatographically over silica gel by means of ether/n-hexane.

Yield: 6.9 g. corresponding to 86.8% of the theoretical yield.

| $C_{11}H_{15}O_4J$ | M.P.: <0° C. |
|---|---|
| Mol. weight: 338.17 | $[\alpha]_8^{20}$: −28.8° (in methanol) |

Step 2.5

Preparation of 3β-acetoxy methyl-8β-methoxy-10β-methyl-2,9-DTD-4-one of Formula 2.5

To 20 g. of the compound of Formula 2.4 dissolved in 100 ml. of dimethyl formamide, there are added 20 g. of tetraethyl ammonium acetate. The mixture is heated to 110° C. for four hours, while stirring. Thereupon, the solvent is distilled off, the residue is taken up in water and is extracted with ether. The combined organic phases are dried over sodium sulfate, filtered, and concentrated by evaporation in a vacuum.

Yield: 9.5 g. corresponding to 66% of the theoretical yield.

| $C_{13}H_{18}O_6$ | M.P.: <0° C. |
|---|---|
| Mol. weight: 270.28 | $[\alpha]_8^{20}$: −50.9° (in methanol) |

Step 2.6

Preparation of 3β-hydroxy methyl-4α-hydroxy-8β-methoxy-10β-methyl-2,9-DTD of Formula 2.6

9.5 g. of the compound of Formula 2.5 in 100 ml. of absolute tetrahydrofurane are added drop by drop to a suspension of 2.8 g. of lithium aluminum hydride LiAlH4 in 100 ml. of absolute tetrahydrofurane at 0° C. in a nitrogen atmosphere while stirring. Stirring of the solution is then continued at room temperature for one more hour.

To the resulting hydrogenation mixture there are added first 50 ml. of moist ether and later on about 5 ml. of water. The precipitated salts are filtered off and the filtrate is concentrated by evaporation in a vacuum. The residue is taken up in saturated ammonium sulfate solution and extracted with dichloro methane. The combined organic phases are dried over sodium sulfate, filtered, and concentrated by evaporation in a vacuum.

Yield: 4.1 g. corresponding to 50.6% of the theoretical yield.

The resulting compound of Formula 2.6 has proved to be identical with the compound of Formula 1.5 obtained by proceeding as described in Example 1.

EXAMPLE 3

This example describes the procedure followed according to Process 3.

Step 3.1

Preparation of 3β-iodo methyl-4β-(tetrahydropyranyl-2)-8β-methoxy-10β-methyl-2,9-DTD of Formula 3.1

To 43.4 g. of the compound of Formula 2.3, obtained according to Example 2, in 300 ml. of dichloro methane there are added 17 ml. of 3,4-dihydro-2H-pyrane and a small amount (spatula tip full) of picric acid. The mixture is stirred at room temperature for one hour. The reaction mixture is then twice agitated with a saturated sodium bicarbonate solution and is twice washed with water. The dichloro methane phase is dried over sodium sulfate, filtered, and concentrated by evaporation in a vacuum.

Yield: 53.15 g. corresponding to 98.2% of the theoretical yield.

| $C_{16}H_{25}JO_5$ | M.P.: 95-97° C. |
|---|---|
| Mol. weight: 424.27 | $[\alpha]_D^{20}$: +35.3° (in methanol) |

Step 3.2

Preparation of 3β-acetoxy methyl-4β-hydroxy-8β-methoxy-10β-methyl-2,9-DTD of Formula 3.2

20 g. of tetrabutyl ammonium acetate and 40 g. of potassium acetate are added to 42.4 g. of the compound of Formula 3.1 in 300 ml. of dimethylformamide. The mixture is heated to 120° C. for five hours, while stirring. Thereupon the solvent is distilled off in a vacuum and the residue is dissolved in dichloro methane. The organic solvent solution is washed twice with water, dried over sodium sulfate, filtered, and concentrated by evaporation in a vacuum. The residue is dissolved in 200 ml. of methanol. 100 ml. of 1 N hydrochloric acid solution are added thereto and the mixture is stirred at room temperature for two hours. Thereafter the solution is concentrated by careful evaporation to a volume of about 100 ml.

The aqueous phase is twice extracted, each time with 100 ml. of dichloro methane. The combined organic phases are dried over sodium sulfate, filtered, and concentrated by evaporation in a vacuum.

| $C_{14}H_{20}O_6$ | M.P.: <0° C. |
|---|---|
| Mol. weight: 284.31 | $[\alpha]_D^{20}$: −23.9° (in methanol) |

Step 3.3

Preparation of 3β-acetoxy-8β-methoxy-10β-methyl-2,9-DTD-4-one of Formula 3.3

55 ml. of Jones reagent (chromium trioxide and sulfuric acid) are added drop by drop to 28.2 g. of the compound of Formula 3.2 in 500 ml. of acetone at 0° C., while stirring. After completion of the oxidation reaction, 5 ml. of isopropanol are added and the chromium salts are filtered off. The salts are washed with 300 ml. of dichloro methane. The combined organic phases are dried over sodium sulfate, filtered, and concentrated by evaporation in a vacuum.

Yield: 23.1 g. corresponding to 81.9% of the theoretical yield.

The compound obtained as described above proved to be identical with the compound of Formula 2.5 as obtained according to Example 2.

Conversion of said compound of Formula 3.3 into the final compound of Formula 1.5 (2.6) is carried out as described hereinabove in Example 2, step 2.6.

EXAMPLE 4

This example describes the procedure followed according to Process 4.

Step 4.1

Preparation of 3$\beta$-iodo methyl-4$\alpha$-hydroxy-8$\beta$-methoxy-10$\beta$-methyl-2,9-DTD of Formula 4.1

1.5 g. of sodium borohydride suspended in 10 ml. of absolute tetrahydrofurane are added to 3.3 g. of the 3$\beta$-iodo methyl-4-ketone compound of Formula 2.4 in 20 ml. of absolute tetrahydrofurane while kept in a nitrogen atmosphere. The reaction requires about one hour and is carried out at room temperature. Thereafter 40 ml. of water are added. The resulting solution is extracted with dichloro methane. The combined organic phases are dried over sodium sulfate, filtered, and concentrated by evaporation in a vacuum. 3.3 g. of a crude product are obtained which, on recrystallization from n-hexane and ether, yield 2.8 g. of the pure compound of the Formula 4.1.

The yield amounts to 84.3% of the theoretical yield.

| $C_{11}H_{17}O_4J$ | M.P.: 75–77° C. |
|---|---|
| Mol. weight: 340.166 | $[\alpha]_D^{20}$: −18.5° (in methanol) |

Step 4.2

Preparation of 3$\beta$-iodo methyl-4$\alpha$-acetoxy-8$\beta$-methoxy-10$\beta$-methyl-2,9-DTD of Formula 4.2

34.0 g. of the compound of Formula 4.1, 50 ml. of acetic acid anhydride, and 5 ml. of pyridine are stirred at 60° C. for one hour. Thereupon the reaction mixture is repeatedly concentrated by evaporation in a vacuum with the addition of toluene. The residue is taken up in water and is extracted with ether. The combined organic phases are dried over sodium sulfate, filtered, and concentrated by evaporation in a vacuum.

Yield: 34.9 g. corresponding to 91.4% of the theoretical yield.

| $C_{12}H_{19}O_5J$ | M.P.: 109–111° C. |
|---|---|
| Mol. weight: 382.2 | $[\alpha]_D^{20}$: −4.5° (in methanol) |

Step 4.3

Preparation of 3$\beta$-acetoxy methyl-4$\alpha$-acetoxy-8$\beta$-methoxy-10$\beta$-methyl-2,9-DTD of Formula 4.3

15 g. of tetrabutyl ammonium acetate and 50 g. of anhydrous sodium acetate are added to 34.9 g. of the compound of Formula 4.2 in 600 ml. of analytically pure dimethyl formamide. The mixture is heated to 150° C. for seven hours, while stirring. Thereupon the solvent is distilled off in a vacuum and the residue is taken up in water. After extraction with ether, the combined ethereal phases are dried over sodium sulfate, filtered, and concentrated by evaporation in a vacuum.

Yield: 24.9 g. corresponding to 86.7% of the theoretical yield.

| $C_{15}H_{22}O_7$ | M.P.: <0° C. |
|---|---|
| Mol. weight: 314.346 | $[\alpha]_D^{20}$: −29.3° (in methanol) |

Step 4.4

Preparation of 3$\beta$-hydroxy methyl-4$\alpha$-hydroxy-8$\beta$-methoxy-10$\beta$-methyl-2,9-DTD of Formula 4.4

2.3 g. of sodium hydroxide in 40 ml. of methanol are added to 8.7 g. of the compound of Formula 4.3 in 100 ml. of ether. The mixture is stirred at room temperature for one hour. The resulting solution is then adjusted to a pH of 7 by the addition of glacial acetic acid and concentrated by evaporation in a vacuum. The residue is taken up in saturated aqueous ammonium sulfate solution and is extracted with dichloro methane. The combined organic phases are dried over sodium sulfate, filtered, and concentrated by evaporation in a vacuum. The yield of crude reaction product amounts to 6.2 g. After recrystallization from ether and hexane, there are obtained 5.6 g. of the pure compound of Formula 4.4 which corresponds to a yield of 80.4% of the theoretical yield.

The resulting compound of Formula 4.4 proved to be identical with the compounds of Formulas 1.5 and 2.6 as obtained when proceeding according to Examples 1 and 2.

EXAMPLE 5

When proceeding as described hereinabove in Example 1, steps 1.1 to 1.5, but replacing the methanol by ethanol in step 1.2 of Example 1, there are obtained the following 8$\beta$-ethoxy compounds:

In step 5.1

3$\beta$-Acetoxy methyl-4$\beta$-acetoxy-8$\beta$-ethoxy-10-methylene-2,9-DTD

| $C_{16}H_{22}O_7$ | M.P.: <0° C. |
|---|---|
| Mol. weight: 326.35 | $[\alpha]_D^{20}$: +9.4° (in methanol) |

In step 5.2

3$\beta$-Hydroxy methyl-4$\beta$-hydroxy-8$\beta$-ethoxy-10$\beta$-methyl-2,9-DTD.

| $C_{12}H_{20}O_5$ | M.P.: 56–57° C. |
|---|---|
| Mol. weight: 244.29 | $[\alpha]_D^{20}$: −26.0° (in methanol) |

In step 5.3

3$\beta$-Hydroxy methyl-8$\beta$-ethoxy-10$\beta$-methyl-2,9-DTD-4-one

| $C_{12}H_{18}O_5$ | M.P.: <0° C. |

In step 5.4

3β-Hydroxy methyl-4α-hydroxy-8β-ethoxy-10β-methyl-2,9-DTD

| | |
|---|---|
| $C_{12}H_{20}O_5$ | M.P.: 86–87° C. |
| Mol. weight: 244.29 | $[\alpha]_D^{20}$: −56.3° (in methanol) |

EXAMPLE 6

When proceeding as described hereinabove in Example 2, steps 2.1 and 2.3 to 2.6, replacing the methanol by ethanol in step 2.1, and omitting the hydrogenation step 2.2, the following 8β-ethoxy-10-methylene compounds are obtained:

In step 6.1

3β-ido methyl-4β-acetoxy-8β-ethoxy-10-methylene-2,9-DTD

| | |
|---|---|
| $C_{14}H_{19}O_5J$ | M.P.: 63–65° C. |
| Mol. weight: 394.21 | $[\alpha]_D^{20}$: +76° (in methanol) |

In step 6.2

3β-iodo methyl-4β-hydroxy-8β-ethoxy-10-methylene-2,9-DTD

| | |
|---|---|
| $C_{12}H_{17}O_4J$ | M.P.: <0° C. |
| Mol. weight: 352.17 | $[\alpha]_D^{20}$: +18.0° (in methanol) |

In step 6.3

3β-iodo methyl-8β-ethoxy-10-methylene-2,9-DTD-4-one

| | |
|---|---|
| $C_{12}H_{15}O_4J$ | M.P.: <0° C. |
| Mol. weight: 350.16 | $[\alpha]_D^{20}$: −3.3° (in methanol) |

In step 6.4

3β-acetoxy methyl-8β-ethoxy-10-methylene-2,9-DTD-4-one

| | |
|---|---|
| $C_{14}H_{18}O_6$ | M.P.: <0° C. |
| Mol. weight: 282.29 | $[\alpha]_D^{20}$: −8.0° (in methanol) |

In step 6.5

3β-hydroxy methyl-4α-hydroxy-8β-ethoxy-10-methylene-2,9-DTD

| | |
|---|---|
| $C_{12}H_{18}O_5$ | M.P.: <0° C. |
| Mol. weight: 242.27 | $[\alpha]_D^{20}$: +25.9° (in methanol) |

EXAMPLE 7

When proceeding as described hereinabove in Example 2, steps 2.1 to 2.4, and in Example 4, steps 4.1 to 4.4, and replacing the methanol in step 2.1 by ethanol, there are obtained the following 8β-ethoxy-10β-methyl compounds:

In step 7.1

3β-iodo methyl-4β-acetoxy-8β-ethoxy-10-methylene-2,9-DTD

| | |
|---|---|
| $C_{14}H_{19}O_5J$ | M.P.: 63–65° C. |
| Mol. weight: 394.21 | $[\alpha]_8^{20}$: +76° (in methanol) |

In step 7.2

3β-iodo methyl-4β-acetoxy-8β-ethoxy-10β-methyl-2,9-DTD

| | |
|---|---|
| $C_{14}H_{21}O_5J$ | M.P.: 103–105° C. |
| Mol. weight: 369.228 | $[\alpha]_D^{20}$: +20.7° (in methanol) |

In step 7.3

3β-iodo methyl-4β-hydroxy-8β-ethoxy-10β-methyl-2,9-DTD

| | |
|---|---|
| $C_{12}H_{18}O_4J$ | M.P.: 83–85° C. |
| Mol. weight: 353.18 | $[\alpha]_D^{20}$: −41.2° (in methanol) |

In step 7.4

3β-iodo methyl-8β-ethoxy-10β-methyl-2,9-DTD-4-one

| | |
|---|---|
| $C_{12}H_{16}O_4J$ | M.P.: 58–59° C. |
| Mol. weight: 351.173 | $[\alpha]_D^{20}$: −32.1° (in methanol) |

In step 7.5

3β-iodo methyl-4α-hydroxy-8β-ethoxy-10β-methyl-2,9-DTD

| | |
|---|---|
| $C_{12}H_{18}O_4J$ | M.P.: <0° C. |
| Mol. weight: 353.18 | $[\alpha]_D^{20}$: −16.7° (in methanol) |

In step 7.6

3β-iodo methyl-4α-acetoxy-8β-ethoxy-10β-methyl-2,9-DTD

| | |
|---|---|
| $C_{14}H_{20}O_5J$ | M.P.: <0° C. |
| Mol. weight: 395.218 | $[\alpha]_D^{20}$: −6.5° (in methanol) |

In step 7.7

3β-acetoxy methyl-4α-acetoxy-8β-ethoxy-10β-methyl-2,9-DTD

| | |
|---|---|
| $C_{16}H_{24}O_7$ | M.P.: 70–72° C. |
| Mol. weight: 328.36 | $[\alpha]_D^{20}$: +27.5° (in methanol) |

In step 7.8

3β-hydroxy methyl-4α-hydroxy-8β-ethoxy-10β-methyl-2,9-DTD

| C₁₂H₂₀O₅ | M.P.: 86–87° C. |
|---|---|
| Mol. weight: 244.29 | $[\alpha]_D^{20}$: −56.3° |

This compound corresponds to the compound obtained according to Example 5, step 5.4.

EXAMPLE 8

When proceeding according to Example 2, steps 2.1, 2.3, and 2.4 followed by the process steps 4.1 to 4.4 of Example 4 and omitting the hydrogenation step 2.2 of Example 2, there are obtained the following 8β-methoxy-10-methylene compounds:

In step 8.1 corresponding to step 2.1

3β-iodo methyl 4β-acetoxy-8β-methoxy-10-methylene-2,9-DTD

| C₁₃H₁₇O₅J | M.P.: 104–106° C. |
|---|---|
| Mol. weight: 380.19 | $[\alpha]_D^{20}$: +68° (in methanol) |

In step 8.2

3β-iodo methyl-4β-hydroxy-8β-methoxy-10-methylene-2,9-DTD

| C₁₁H₁₅O₄J | M.P.: <0° C. |
|---|---|
| Mol. weight: 338.25 | $[\alpha]_D^{20}$: +13° (in methanol) |

In step 8.3

3β-iodo methyl-8β-methoxy-10-methylene-2,9-DTD-4-one

| C₁₁H₁₃O₄J | M.P.: <0° C. |
|---|---|
| Mol. weight: 336.1 | |

In step 8.4

3β-iodo methyl 4α-hydroxy-8β-methoxy-10-methylene-2,9-DTD

| C₁₁H₁₅O₄J | M.P.: 108–110° C. |
|---|---|
| Mol. weight: 338.15 | $[\alpha]_D^{20}$: +10° (in methanol) |

In step 8.5

3β-iodo methyl-4α-acetoxy-8β-methoxy-10-methylene-2,9-DTD

| C₁₃H₁₇O₅J | M.P.: 122–124° C. |
|---|---|
| Mol. weight: 380.17 | $[\alpha]_D^{20}$: +28.7° (in methanol) |

In step 8.6

3β-acetoxy methyl-4α-acetoxy-8β-methoxy-10-methylene-2,9-DTD

| C₁₅H₂₀O₇ | M.P.: 83–85° C. |
|---|---|
| Mol. weight: 312.33 | $[\alpha]_D^{20}$: +24.6° (in methanol) |

In step 8.7

3β-hydroxy methyl-4α-hydroxy-8β-methoxy-10-methylene-2,9-DTD

| C₁₁H₁₆O₅ | M.P.: <0° C. |
|---|---|
| Mol. weight: 228.25 | $[\alpha]_D^{20}$: +22.3° (in methanol) |

EXAMPLE 9

By proceeding as described in Example 7 but replacing the methanol by n-butanol, there is obtained the corresponding 8β-n-butoxy compound:

3β-hydroxy methyl-4α-hydroxy-8β-n-butoxy-10β-methyl-2,9-DTD

| C₁₄H₂₄O₅ | M.P. : <0° C. |
|---|---|
| Mol. weight: 272.2 | $[\alpha]_D^{20}$ : −40.7° (in methanol) |

Of course, many changes and variations, for example, in the reaction conditions, the reaction temperature and duration, the reactants and solvents used, the methods of working up the reaction mixtures and of purifying the reaction products, and the like, may be made by those skilled in the art in accordance with the principles set forth herein and in the claims annexed hereto.

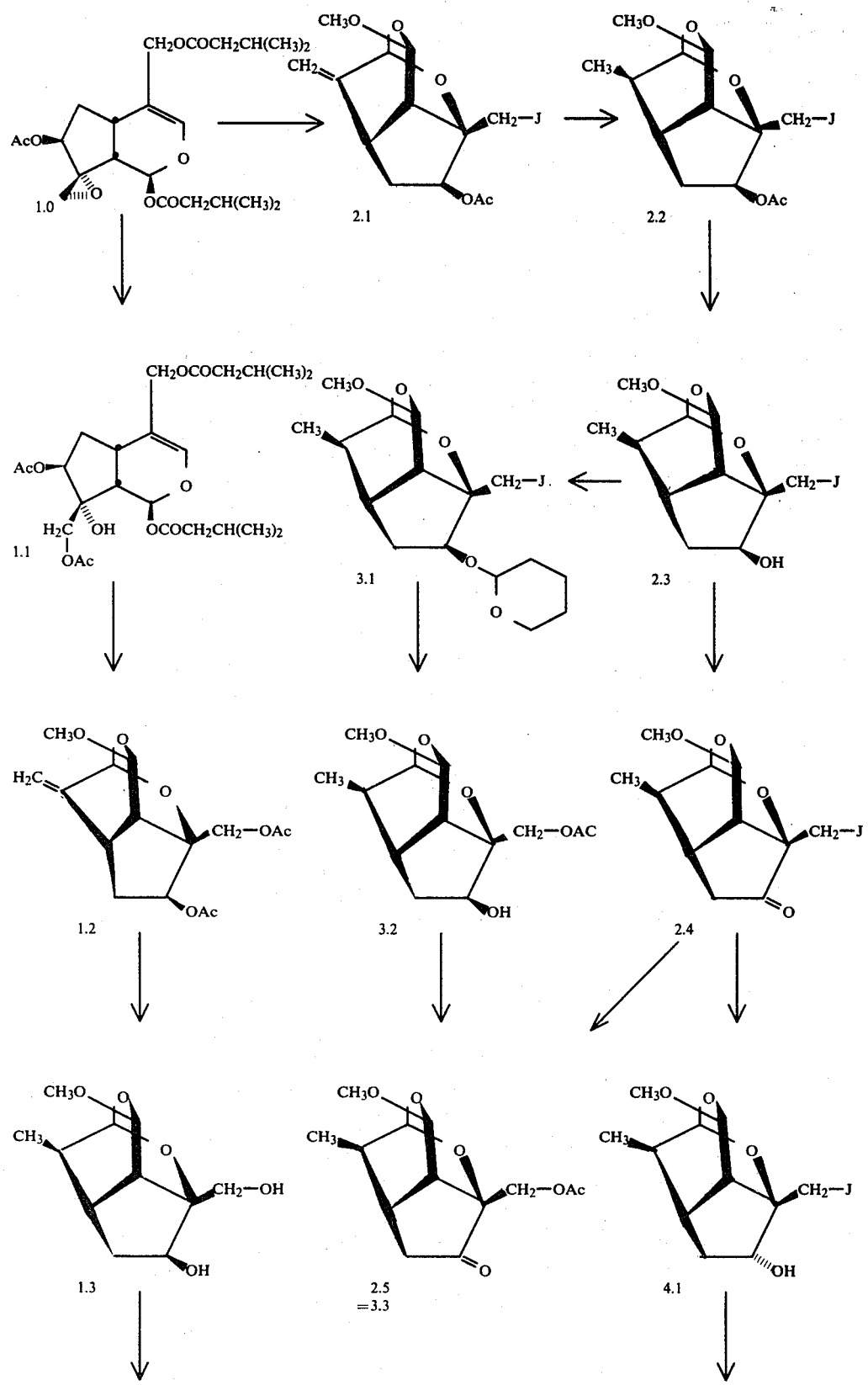

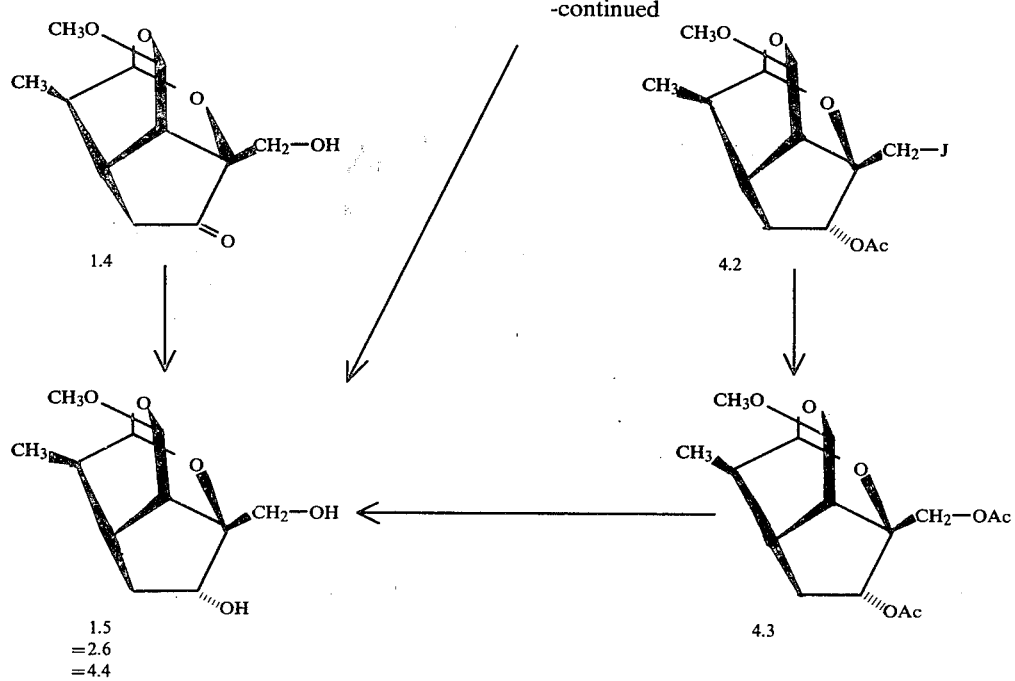

It is claimed:

1. A 3β-hydroxy methyl-4α-hydroxy-3β-alkoxy-2,9-dioxa tricyclo[4,3,1,0$^{3,7}$]decane of the formula

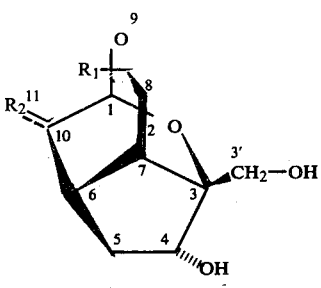

in which
R$_1$ indicates an alkoxy group and
R$_2$ indicates 10-methylene or 10β-methyl.

2. The compound of claim 1, in which
R$_1$ is a lower alkoxy group.

3. The compound of claim 1, in which
R$_1$ is a lower alkoxy group with 1 to 4 carbon atoms and
R$_2$ is the methylene group.

4. The compound of claim 1, in which
R$_1$ is a lower alkoxy group with 1 to 4 carbon atoms and
R$_2$ is the methyl group in β-position.

5. The compound of claim 1, in which
R$_1$ is methoxy and
R$_2$ is methylene, said compound being 3β-hydroxy methyl-4α-hydroxy-8β-methoxy-10-methylene-2,9-dioxa tricyclo[4,3,1,0$^{3,7}$]decane.

6. The compound of claim 1, in which
R$_1$ is methoxy and
R$_2$ is methyl in β-position, said compound being 3β-hydroxy methyl-4α-hydroxy-8β-methoxy-10β-methyl-2,9-dioxa tricyclo[4,3,1,0$^{3,7}$]decane.

7. The compound of claim 1, in which
R$_1$ is ethoxy and
R$_2$ is methylene, said compound being 3β-hydroxy methyl-4α-hydroxy-8β-ethoxy-10-methylene-2,9-dioxa tricyclo[4,3,1,0$^{3,7}$]decane.

8. The compound of claim 1, in which
R$_1$ is ethoxy and
R$_2$ is methyl in β-position, said compound being 3β-hydroxy methyl-4α-hydroxy-8β-ethoxy-10β-methyl-2,9-dioxa tricyclo[4,3,1,0$^{3,7}$]decane.

9. The compound of claim 1, in which
R$_1$ is n-butoxy and
R$_2$ is methyl in β-position, said compound being 3β-hydroxy methyl-4α-hydroxy-8β-n-butoxy-10β-methyl-2,9-dioxa tricyclo[4,3,1,0$^{3,7}$]decane.

10. A composition of matter for inducing sleep in mammals, comprising a sleep-inducing amount of a 3β-hydroxy methyl-4α-hydroxy-8β-alkoxy-2,9-dioxa tricyclo[4,3,1,0$^{3,7}$]decane as defined in claim 1, and a pharmacologically inert diluent material.

11. A method of inducing sleep in mammals, comprising the step of administering to a mammal a sleep-inducing amount of a compound as defined in claim 1.

* * * * *